(12) United States Patent
Huber et al.

(10) Patent No.: US 6,524,815 B1
(45) Date of Patent: Feb. 25, 2003

(54) VE-CADHERIN PROMOTER AND ITS USES

(75) Inventors: Philippe Huber, Seyssins (FR); Monique Laurent, Grenoble (FR); Sylvie Gory, Saint-Egreve (FR)

(73) Assignee: Commissariat a l'Energie Atomique-C.E.A., Paris (FR)

(*) Notice: Subject to any disclaimer, the term of this patent is extended or adjusted under 35 U.S.C. 154(b) by 0 days.

(21) Appl. No.: 09/319,284

(22) PCT Filed: Dec. 2, 1997

(86) PCT No.: PCT/FR97/06178

§ 371 (c)(1),
(2), (4) Date: Aug. 27, 1999

(87) PCT Pub. No.: WO98/24892

PCT Pub. Date: Jun. 11, 1998

(30) Foreign Application Priority Data

Dec. 3, 1996 (FR) ............................................. 96 14801

(51) Int. Cl.[7] ........................ C12P 21/06; C12N 15/63; C12N 5/06; C07H 21/04

(52) U.S. Cl. .................... 435/69.1; 435/320.1; 435/455; 435/456; 435/458; 435/355; 435/372; 536/23.1; 536/24.2

(58) Field of Search ........................... 800/25; 536/23.1, 536/24.2; 435/320.1, 69.1, 325, 355, 372, 455, 456, 458; 514/44

(56) References Cited

FOREIGN PATENT DOCUMENTS

WO  WO 96/09381  3/1996

OTHER PUBLICATIONS

R. J. Wall, Transgenic livestock: Progress and prospects for the future, 1996, Theriogenology, vol. 45, pp. 57–68.*

Strojek et al., The use of transgenic animal techniques for livestock improvement, 1988, Genetic Engineering: Principles and Methods, vol. 10, pp. 221–246.*

Hammer et al., Genetic engineering of mammalian embryos, 1986, J. Anim. Sci., vol. 63, pp. 269–278.*

Ebert et al., A moloney MLV–Rat somatotropin fusion gene produces biologically active somatotropin in a transgenic pig, 1988, Molecular Endocrinology, vol. 2, pp. 277–283.*

Kappel et al., Regulating gene expression in transgenic animals, 1992, Current Opinion in Biotechnology, vol. 3, pp. 548–553.*

Miller et. al.; Targeted vectors for gene therapy, 1995, FASEB J. 9: 190–199.*

Deonarain; Ligand–targeted receptor–mediated vectors for gene delivery, 1998, Exp. Opin. Ther. Patents 8(1): 53–69.*

Verma et. al.; Gene therapy–promises, problems and prospects, 1997, Nature vol. 389: 239–242.*

Ngo et. al.; Computational Complexity, Protein Structure Prediction, and the Levinthal Paradox, 1994. In The Protein Folding Problem and Tertiary Structure Prediction (Merz, K. et al., Eds.), Birkhauser, Boston, pps.*

Rudinger; Characteristics of the amino acids as components of a peptide hormone sequence, 1976. In Peptide Hormones (Parsons, J.A., Ed) University Park Press, Baltimore, pp. 1–7.*

Moreadith et al. Gene targeting in embryonnic stem cells: the new physiology and metabolism. J. Mol. Med. 75:208–216, 1997.*

Seamark, R.F. Progress and emerging problems in livestock transgenesis: a Summary perspective. Reprod. Fertil. Dev. 6:653–657, 1994.*

Dang, C.V. et al. Gene therapy and translational cancer research. Clin. Cancer Res. 5:471–474, 1999.*

Wivel, N.A. & Wilson, J.M. Methods of gene delivery. Hematol. Oncol. Clin. North Am. 12:483–501. 1998.*

Mullins, L.J. & Mullins, J.J. Transgenesis in the rat and larger mammals. J. Clin. Invest. 98:S37–S40, 1996.*

Shen, J et al. (1995) Transgenic rabbits with the integrated human 15–lipoxygenase gene driven by a lysozyme promoter: macrophage–specific expression and variable positional specificity of the transgenic enzyme. FASEB J. 9:1623–1631. (Abstract Only).

Hammer, RE et al. (Nov. 1990) Spontaneous inflammatory disease in transgenic rats expressing hla–b27 and human 2m: an animal model of hla–b27–associated human disorders. Cell 63:1099–1112. (Abstract Only).

Sandgren EP et al. (Sep. 1995). Inhibition of Mammary Gland Involution is Associated with Transforming Growth Factor Alpha but not c–myc–induced Tumorigenesis in Transgenic Mice. Cancer Res. 55(17): 3915–3927 (Abstract Only).

Hondu, H et al. (May 1995) Expression of p210bcr/ab1 By Metallothionein Promoter Induced T–cell Leukemia in Transgenic Mice. Blood 85(10):2853–2861 (Abstract Only).

Shiota, G et al. (Oct. 1995) Characterization of Double Trangenic Mice Expressing Hepatocye Growth Factor and Transforming Growth Factor Alpha. Res. Commun. Mol. Pathol. Pharmacol. 90(1):17–24 (Abstract Only).

(List continued on next page.)

*Primary Examiner*—Dave T. Nguyen
*Assistant Examiner*—Quang Nguyen
(74) *Attorney, Agent, or Firm*—Morgan, Lewis & Bockius LLP

(57) ABSTRACT

The invention relates to the isolation and cloning of the VE-cadherin promoter. It also relates to transformed cells and transgenic animals containing the VE-cadherin promoter. The VE-cadherin promoter of the invention is particularly useful for the tissue-specific expression of a gene of interest in the vascular endothelium.

12 Claims, 2 Drawing Sheets

OTHER PUBLICATIONS

Neule, GA et al. (Oct. 1995) Ectopic Expression of Rhombotin–2 Causes Selective Expansion of CD4–CD8–Lymphocytes in the Thymus and T–cell tumors in Transgenic Mice. Blood 86(8): 3060–3071 (Abstract Only).

Hanania, EG et al, (Dec. 1995) Regulation of Retinoblastoma Gene Expression in a Mouse Mammary Tumor Model. Cancer Gene Ther. 2(4):251–261 (Abstract Only).

Lin, CS, et al. (Dec. 1995) Expression of Rabbit C–reactive Protein in Transgenic Mice. Immunol. Cell Biol. 73(6):521–531 (Abstract Only).

Murphy, LJ et al, (Dec. 1995) Expression of Human Insulin-–like Growth Factor–binding Protein–3 in Transgenic Mice. J. Mol. Endocrinol. 15(3):293–303 (Abstract Only).

van Denderen, BJ et al. (Feb. 1996) Expression of Functional Decay–accelerating Factor (CD5) In Transgenic Mice Protects Against Human Complement–mediated Attack. Transplantation 61(4):582–588 (Abstract Only).

Morita, A et al. (Mar. 1994) TL Antigen as a Transplantation Antigen Recognized by TL–restricted Cytotoxic T Cells. J. Exp Med. 179(3):777–784 (Abstract Only).

Rashid–Doubell, F et al. (1994) Effects of Basic Fibroblast Growth Factor and Gamma Interferon on Hippocampal Progenitor Cells Derived from the H–2Kb–tsA58 Transgenic Mouse. Gene Ther. 1(Suppl 1):S63 (Abstract Only).

Fujita, K et al. (Feb. 1993) B Cell Development Is Perturbed in Bone Marrow from c–fos/v–jun doubly Transgenic Mice. Int. Immunol. 5(2):227–230 (Abstract Only).

Morello, D et al. (Jun. 1990) c–myc, c–fos. and c–jun Regulation in the Regenerating Livers of Normal and H–2K/c–myc Transgenic Mice. Mol. Cell Biol. 10(6):3185–3193 (Abstract Only).

Swanson, ME et al. (May 1992) Production of Functional Human Hemoglobin in Transgenic Swine. Biotechnology 10(5):557–559 (Abstract Only).

Rexroad, CE et al. (1989) Production of Transgenic Sheep With Growth–regulating Genes. Mol. Reprod. Dev. 1(3):164–169 (Abstract Only).

Fan, J et al. (Aug. 1994) Overexpression of Hepatic Lipase in Transgenic Rabbits Leads to a Marked Reduction of Plasma High Density Lipoproteins and Intermediate Density Lipoproteins. Proc. Natl. Acad. Sci. (USA) 91:8724–8728 (Abstract Only).

Velander, WH et al. (Dec. 1992) High–level Expression of a Heterologous Protein in the Milk of Transgenic Swine Using the cDNA Encoding Human Protein C. Proc. Natl. Acad. Sci. (USA) 89(24):12003–12007 (Abstract Only).

Ebert, KM et al. (Sep. 1991) Transgenic Production of a Variant of Human Tissue–type Plasminogen Activator in Gnat Milk: Generation of Transgenic Goats and Analysis of Expression. Biotechnology 9(9):835–838 (Abstract Only).

Jallat, S et al. (Oct. 1990) Characterization of Recombinant Human Factor IX Expressed in Transgenic Mice and in Derived Trans–immortalized Hepatic Cell Lines. EMBO J. 9(10):3295–3301 (Abstract Only).

Bischoff, R et al. (Jul. 1992) A 17.6 kbp Region located Upstream of the Rabbit WAP Gene Directs High Level Expression of a Functional Human Protein Variant in Transgenic Mouse Milk. FEBS Letters 305(3):265–268 (Abstract Only).

Perraud, F et al. (May 1992) The Promoter of the Human Cystic Fibrosis Transmembrane Conductance Regulator Gene Directing SV40 T Antigen Expression Induces Malignant Proliferation of Ependymal Cells in Transgenic Mice. Oncogene 7(5):993–997 (Abstract Only).

Fodor, WL et al. (Nov. 1994) Expression of a Functional Human Complement Inhibitor in a Transgenic Pig as a Model for the Prevention of Xenogeneic Hyperacute Organ Rejection. Proc. Natl. Acad. Sci. (USA) 91:11153–11157 (Abstract Only).

Brem, G et al. (Nov. 1994) Expression of Synthetic cDNA Sequences Encoding Human Insulin–like Growth Factor–1 (IGF–1) In the Mammary Gland of Transgenic Rabbits. Gene 149(2):351–355 (Abstract Only).

Limenta, JM et al. (May 1995) Transgenic Rabbits as Bioreactors for the Production of Human Growth Hormone. J. Biotechnol. 40(1):49–58 (Abstract Only).

Massoud, M et al. (May 1991) Expression of Active Recombinant Human Alpha 1–antitrypsin in Transgenic Rabbits. J. Biotechnol. 18(3):193–203 (Abstract Only).

Snyder, BW et al. (Apr. 1995) Developmental and Tissue–Specific Expression of Human CD4 in Transgenic Rabbits. Mol. Reprod. Dev. 40(4):419–428 (Abstract Only).

Gillespie, FP et al. (May 1993) Tissue–specific Expression of Human CD4 in Transgenic Mice. Mol. Cell Biol. 13(5):2952–2958 (Abstract Only).

Breviario et al., Functional properties of human vascular endothelial cadherin (7B4/Cadherin–5), an endothelium–specific cadherin, Arterioscler. Thromb. Vasc. Biol. 15:1229–1239 (1995).

Janel et al., Comparison of the 5'–flanking sequences of the human and bovine von Willebrand factor–encoding genes reveals alteration of highly homologous domains with species–specific Alu–type repeats, Gene 167:291–295 (1995).

Abstract of Japanese Patent Application JP940084526, Apr. 22, 1994, "Promoter of Human Flt Gene Encoding Receptor Type Tyrosine Kinase—Useful for Tissue Specific Expression of Heterologous Proteins".

Philippe Huber, et al.; "Genomic Structure and Chromosomal Mapping of the Mouse VE–Cadherin Gene (Cdh5)"; Genomics, vol. 32, Nov. 28, 1995, pp. 21–28.

William C. Aird, et al.; "Human von Willebrand factor gene sequences target expression to a subpopulation of endothelial cells in transgenic mice"; Proc. Natl. Acad. Sci. USA, vol. 92, 1995; pp. 4567–4571.

Thursten M. Schlaeger, et al.; "Vascular endothelial cell lineage–specific promoter in transgenic mice"; Development, vol. 121 Jan. 3, 1995; pp. 1089–1098.

* cited by examiner

SEQUENCE LISTING

<160> NUMBER OF SEQ ID NOS: 3

<210> SEQ ID NO 1
<211> LENGTH: 2509

```
<212> TYPE: DNA
<213> ORGANISM: Mus musculus

<400> SEQUENCE: 1
actagtagca gaaacaaggt cctctggaag agcaactgat gctcttaggt actgaagcat       60
catcctgccc cagagaccac tcgcatatga agcacacata ttcagtctgc cttacttgtg      120
ttaatgattg ccagtgtccc tctgacctcc tagccctgaa aaggtgtggc ctgaaggtca      180
tttcagagac ggggagagct gctcagagaa gccaatcggc gagtctagga cacacagaca      240
ggatctagtc ccagagttcg ctagcctagg tgagcgtccc ctggcccctt ataccacttc      300
cttctccagc ttgcatctaa ttcgctctgg cagaccatcg tgtttcctgt cttcctggca      360
gcctccagca cgctcagtgc tactccctcg catgcgccct cctcccagta ccttctctga      420
ctccagtggg cttggagtgc gaggaggaag ggtgaggaag gggtgaaatc aggtattgga      480
tccacagggg gtctgaagag cactagcctg ccttttggg actgaacttc tgctatgaag       540
acctccactg ccatccctgg agtccggggc acatccaagg gttgctgtcc atcgtttaac      600
tgtttacaga tgacaacaat gactcgtgtt cggggcagaa atatcaccag gctagagta      660 caaaaggagt ttgcattgat ggccggacag gcctgtccct ggaccagcct gcgacgctga      720
gtatgagacc cagcggaagt gctaccctgg cagacgtgtc actgagtaca cagaccacca      780
aggcaggcag ctctcgggga agctgtctat gctgggccag cccaccttga gggcagggaa      840
cagaacagat tgtggcagag aggaaaatgt ggagcttctg tttgttcaca gacacacgca      900
ctcgcccacg cacgcacgca cgcacgcacg cacgcacgaa tgcacgcacg cagtagttga      960
atgctatgga ttccgctcag agctgagaac agccccagcg acagttccct ggcctctctc     1020
cttactctga tgtcctcatc tgtcttcaca tggtctcagg acgctaatac tccatcctaa     1080
tgtacactcc tttccctggg cctccgttcc agttcagttc tcagaggacc tggagggagt     1140
gattggctac accaactttg ctttcgttca ccaagcccat gtctctactt gggtgtctaa     1200
tgggcatctc caacattacc taccccaaac agaaaaccct ttcttccccc caaccacacc     1260
ccaccctacc cccacagtat tttctccatg cccggaaaga tctgctctct tatggtccct     1320
ctttgcctca ctgaaaagca ggacaagttg gggaacttcc caaactttta tgcatgaaga     1380
aacccaggca atttgccaaa aggtacactc tgggggtctg tcatttactc tgagccagaa     1440
ccctgaaatt tttactaacc catcacataa tgaatgaaga gaatcttttt cttttttttt     1500 tttttcttt tttttggtt tttcgagaca gggtttctct gtatagccct ggctatcctg      1560
gaacacactc tgtagaccag gctggcctcg aactcagaaa tccacctgcc tctgcctccc     1620
gagtgctggg attaaaggcg tgcgccacca cgcctggctg aatgaagaga tcttgacctt     1680
catctcccca gcctcttggt cctgagggac cctggtctac ctactgcttt gctgtcttct     1740
tagctcttct tactttttg ctgactcaga cctatgctca tctccattat acagatgagg     1800
agactgaggc atggatccct ggttggtcca tggtcacgtg aagcccatca cccagtattt     1860
gtaaagtgag atgggccagg ctggtacctt ggaactgaaa ctcacactgc cctacctgga     1920
agaatctgac aggcaaaatc tgctgctgaa agtgattgtc tgtcacgttt ctcagctgcc     1980
cgactctgag aactccacag ccccctttcg ttccaccata ctacagagtc gccacggaaa     2040
gccggctctg tggagaagct gaggtagctg ggtttctgtc tgggttactc tgtccagcga     2100
ggaaacaagt accttagacc cactaagcct ctgctttctg aactgtaaag tgggggatat     2160
gacacctgcc tcccagggat ggctgaatgc tctggcagaa gcttagagcc cccacagcta     2220
```

```
ccctaggct cacagctcct ccgatgagac ctagaattga ggtatgagtt gaatacccca      2280
ggcaggtcca aggcttccac gggcccaggc tgaccaagct gaggccgccc accgtagggc      2340
ttgcctatct gcaggcagct cacaaaggaa caataacagg aaaccatccc gaggggaagt      2400
gggccagggc aagttggaaa acctgcctcc ctcccagcct gggtgtggct cccctctccc      2460
ctcctgaggc aatcaactgt gctctccaca aagctcggcc ctggacaga                  2509
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 2

```
cccggaaaga tctgctctct                                                    20
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:PCR primer

<400> SEQUENCE: 3

```
ctccactcga gtctgtccag ggccgagc                                           28
```

VE-CADHERIN PROMOTER AND ITS USES

BACKGROUND OF THE INVENTION

The present invention relates to a promoter which is active in the vascular endothelium and to its use for expressing genes of interest in this tissue.

The vascular endothelium is a cell monolayer which is formed from approximately a million endothelial cells which are distributed throughout the organism.

The endothelium controls the permeability of the blood vessels to fluids and to blood cells and regulates haemostasis and thrombosis. Change in vascular homeostasis can lead to serious pathologies such as arteriosclerosis, which is a major factor in cardiovascular diseases which constitute the prime cause of death in the Western countries, or the uncontrolled vascular proliferation which is observed, for example, in inflammatory diseases (rheumatoid arthritis), diabetic retinopathy, neoplastic angio-genesis or vascular tumours (angiosarcomas, Kaposi's sarcoma).

There is a large number of possible applications for modulating the responses of the endothelial cells by directing expression of a gene of interest in these cells, with examples of these applications being as follows:

in the case of cardiovascular diseases, direct synthesis by the blood vessel wall of fibrinolytic agents such as the plasminogen activators: uPA and tPA;

controlling vascular proliferation:

either in order to stimulate it, for example in order to recreate an antithrombotic surface after denudation of the blood vessel (arteriosclerosis), and to avoid a restenosis following angioplasty, or in order to promote revascularization of the ischaematized tissues;

or in order to slow it down, for example in order to inhibit neoplastic progression by destroying the vascularization of the cancerous tissues. This can be achieved, for example, by constructing dominant-negative mutants for growth factor receptors (flk-l, flt-1, etc.), or by using antisense RNA.

Furthermore, since the vascular endothelium is in direct contact with the blood, it is readily accessible to gene vectors which are introduced by the venous route, and the products of the genes which it expresses can be secreted directly into the circulating blood. These properties can be exploited in order to achieve the secretion of proteins (coagulation factors, hormones, etc.) into the blood circulation.

Furthermore, on account of their presence in the capillaries, in the whole of the body, the vascular endothelial cells represent a particularly advantageous host for expressing, close to their site of action, cell effectors such as, for example, cytokine receptors or competitors of these receptors.

Finally, the endothelial cells have a lifetime which, in man, can amount to as much as 5 to 20 years [FAN et al.; TIPS, 16, p. 57, (1995)]. Transduced endothelial cells can therefore survive and express a transgene for a relatively long period of time.

Studying the in vivo functions of the vascular endothelium, as well as modifying these functions for a therapeutic purpose, requires the use of animal models which enable the role of each of the proteins expressed by the endothelial cells to be assessed individually, whether it is a matter of overexpressing or under-expressing a protein which is produced naturally by these cells, of assessing the activity of novel, potentially therapeutic molecules, or of studying the functional consequences of expressing a heterologous protein.

In order to be in a position to use effectively the potential advantages offered by transferring genes into the vascular endothelium, it is necessary to have available vectors which make it possible to obtain a stable expression of a gene of interest in the endothelial cells, both in vitro and in vivo; furthermore, this expression should, in certain cases, be specific for this tissue in order to avoid the problems which could result from ubiquitous expression.

A certain number of proteins are currently known which are expressed more or less specifically in the endothelium and whose promoters represent potential candidates for expressing a heterologous gene in a tissue-specific manner: the von Willebrand factor [FERREIRA et al., Biochem. J. 293, p. 641–648, (1993)], PECAM-1 (CD31) [De LISSER et al., Immunol. Today, 15, p. 490, (1994)], preproendothelin 1 [HARATS et al., J. Clin. Invest. 95, p. 1335, (1995)], integrin $\alpha v \beta 3$ [BROOKS et al., Science, 264, p. 569, (1994)], P selectin [PAN and McEVER, J. Biol. Chem. 268, p. 22600, (1993)], VE cadherin [LAMPUGNANI et al., J. Cell. Biol. 118, p. 1511–1522, (1992); BREIER et al., Blood, 87, p. 630–641, (1996)], E selectin [WHITLEY et al., Mol. Cell. Biol., 14, p. 6464, (1994)], vascular endothelial growth factor receptor (Flk-1 or KDR) [MILLAUER et al., Cell. 72, p. 835–846, (1992)] and a tyrosine kinase receptor termed tie-2 [SCHLAEGER et al., Development, 121, p. 1089–1098, (1995)].

Some of the promoters which regulate the expression of the above genes have been cloned and studied in vitro in cell cultures, in particular those for E selectin, the von Willebrand factor and preproendothelin 1 [INOUE et al., J. of Biol. Chem. 264, p. 14954–14959, (1989)]. Even if consensus sequences for binding known transcription factors have been identified in some of these promoters, no sequence responsible for the endothelial specificity of the expression has yet been characterized.

For example, in the case of the preproendothelin promoter, an in vivo expression is observed which is not limited to the endothelium but is found in other cell types such as respiratory and intestinal epithelium and the cells of the vascular tunica media [HARATS et al., J. Clin. Invest., 95, p. 1335, (1995)].

Moreover, in a large number of cases, the observations made in vitro do not reflect the true activity and specificity of the promoter sequence in vivo, especially since it has been reported that, in the case of a heterologous gene, this activity and specificity can differ from those observed with the endogenous gene.

For example, the influence of the tie-2, von Willebrand factor and preproendothelin promoter regions on expression of a reporter gene has been studied in vivo in transgenic mice.

Thus, SCHLAEGER et al., [Development 121, p. 1089–1098, (1995)] have observed that the tie-2 promoter, which, in the case of the endogenous gene, is active during vascular proliferation in the embryo or in the adult, behaves differently when it is linked to a heterologous gene; it remains active during the development of the vascularization of the mouse embryo, but is no longer active in the adult, even during angiogenesis.

Using the von Willebrand factor promoter, it was only possible to express the marker gene in some brain endothelial cells; on the other hand, the heterologous gene was expressed in other tissues in which the endogenous gene is not normally expressed [AIRD et al., Proc. Natl. Acad. Sci. USA, 92, p. 4567–4571, (1995)].

Previous research in which the inventors participitated resulted in the isolation of genomic clones containing the gene for VE cadherin and in the determination of the positions of the introns and exons [HUBER et al., Genomics, 32, p. 21–28, (1996)] However, the work did not reveal any sequence controlling the transcription of this gene.

DETAILED DESCRIPTION OF THE INVENTION

Figure 1:
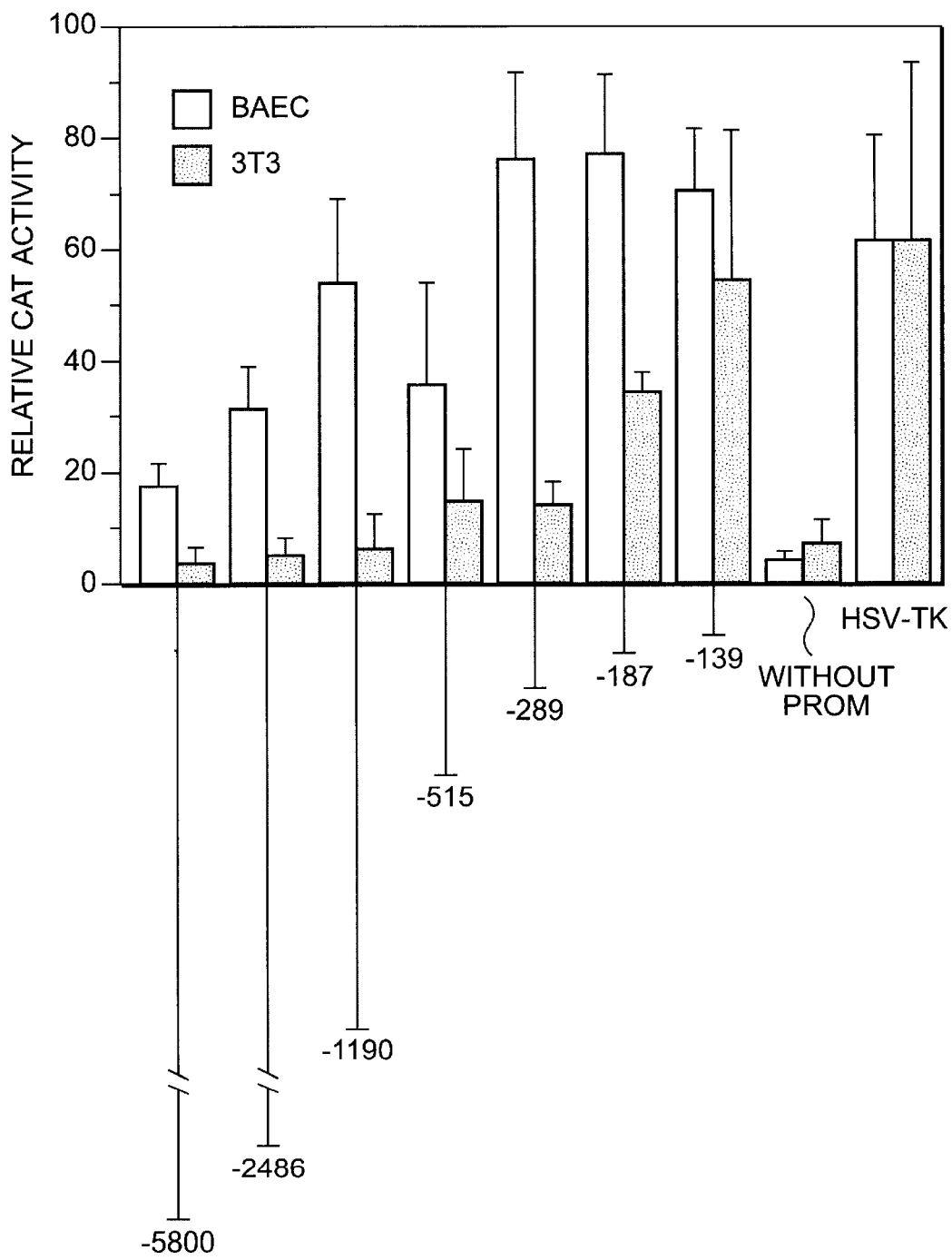
FIG. 1 depicts the CAT activity of the constructs containing the different restriction fragments in BAEC and 3T3 cells.

The inventors have now identified and cloned the sequences of the VE cadherin promoter and have furthermore located regions of this promoter which are responsible for the tissue-specific expression in endothelial cells.

The present invention relates to a nucleic acid molecule whose sequence is that of the VE cadherin promoter, or of a fragment of this promoter.

According to a preferred embodiment of the present invention, the said fragment comprises at least one functional domain which is involved in the activity of the said promoter.

Within the meaning of the present invention, "VE cadherin promoter" is understood as being a nucleic acid sequence which essentially consists of the elements which are required for controlling initiation of the transcription of the VE cadherin gene by a mechanism which is similar to the natural mechanism; "functional domain which is involved in the activity of the VE cadherin promoter" is understood as being either a region of the said promoter which comprises the sequences which are required for initiating transcription or a region of the said promoter which comprises sequences which are involved in regulating transcription initiation in cis.

Nucleic acid molecules which are in accordance with the invention and which constitute a VE cadherin promoter, as defined above, are represented, in particular, by:
  a nucleic acid fragment whose sequence extends from position+22 to position −2486 in relation to the transcription initiation site of the mouse VE cadherin gene; this sequence is depicted in the annexed sequence listing under the number SEQ ID NO: 1; positions 1 to 2509 of the sequence SEQ ID NO: 1 correspond to positions −2486 to +22 as defined in relation to the transcription initiation site of the mouse VE cadherin gene;
  nucleic acid fragments which include the preceding fragment, for example a nucleic acid fragment whose sequence extends from position +22 to position −5800 in relation to the transcription initiation site of the mouse VE cadherin gene.

Nucleic acid molecules which are in accordance with the invention and which contain at least one functional domain, as defined above, of the VE cadherin promoter are represented, in particular, by:
  a) nucleic acid fragments which contain the sequences which are required for initiating transcription. The fragment is, for example, a nucleic acid fragment whose sequence extends from position +22 to position −139 in relation to the transcription initiation site of the mouse VE cadherin gene.
  b) nucleic acid fragments which contain sequences which are involved in regulating transcription, in particular with regard to its tissue specificity; the fragment is, in particular:
    a fragment whose sequence extends from position −140 to position −187 in relation to the transcription initiation site of the mouse VE cadherin gene;
    a fragment whose sequence extends from position −188 to position −289 in relation to the transcription initiation site of the mouse VE cadherin gene;
    a fragment whose sequence extends from position −516 to position −2486 in relation to the transcription initiation site of the mouse VE cadherin gene, and subfragments of this fragment whose sequences extend, respectively, from position −516 to position −1190 and from position −1191 to position −2486 in relation to the transcription initiation site of the mouse VE cadherin gene.

These fragments contain sequences which increase the specificity of expression in endothelial cells.

The present invention encompasses the nucleic acid molecules which constitute segments of more than 10 bp, preferably of more than 20 bp, of the above-mentioned fragments; these molecules can, for example, be used as probes for detecting a nucleic acid molecule in accordance with the invention in a mixture of nucleic acids or as primers for carrying out the amplification of this nucleic acid molecule.

It should, of course, be understood that the nucleic acid fragments which are specified above, and which can be obtained from the promoter of the mouse VE cadherin gene, only constitute an illustration of the subject-matter of the invention. The latter also encompasses, in particular, nucleic acid molecules which duplicate the sequences of homologous promoters or functional domains which exist in mice or other animal species and which can be obtained by the skilled person, using standard molecular biology techniques, by screening a genomic library from the animal concerned with the aid of one or more oligonucleotides which is/are more than 20 bp in size and which duplicate(s) all or part of the sequence of one of the abovementioned fragments. Similarly, the skilled person can, using the above-specified fragments which contain at least one functional domain of the VE cadherin promoter, identify the sequences which constitute the functional domains, for example by means of the DNA footprinting technique, by incubating these fragments with nuclear extracts of endothelial cells, as well as with nuclear extracts of cells in which the VE cadherin promoter is inactive. This makes it possible to construct different nucleic acid molecules in accordance with the invention, for example by deleting sequences which are located outside these functional domains, and/or, where appropriate, replacing them with other sequences.

The nucleic acid molecules which contain functional domains of the VE cadherin promoter can be combined, in different combinations, with each other or with functional elements which are derived from promoters other than the VE cadherin promoter in order to obtain promoters which differ from each other in their level of activity and in their degree of specificity.

For example, if the need is to obtain an increased level of activity, without seeking specific expression in endothelial cells, use will be made of a nucleic acid molecule which contains the elements which are required for initiating transcription and which are located in the sequence extending between +22 and position −139 in relation to the transcription initiation site of the mouse VE cadherin gene.

If the need is to increase, at one and the same time, the level of expression and the specificity of expression in endothelial cells, this first molecule (or another nucleic acid molecule which contains the sequences required for initiating transcription) will be combined with a nucleic acid molecule which contains the regulatory elements which are located in the sequence extending from position −140 to position −187 in relation to the transcription initiation site of the mouse VE cadherin gene, and/or with a nucleic acid molecule which contains the regulatory elements which are located in the sequence extending from position −188 to position −289 in relation to the transcription initiation site of the mouse VE cadherin gene.

If the need is to favour the specificity of expression over the level of expression, a nucleic acid molecule which contains the regulatory elements which are located in the sequence extending from position −516 to position −1190 in relation to the transcription initiation site of the mouse VE cadherin gene will be added; in order to obtain promoters which are active in endothelial cells and inactive (that is to say which do not induce expression of a gene beyond the basal level which is observed in the absence of any promoter) in other cell types, this nucleic acid molecule will contain the regulatory elements which are located in the sequence extending from position −516 to position −2486 in relation to the transcription initiation site of the mouse VE cadherin gene.

The promoters which are obtained from the nucleic acid molecules in accordance with the present invention can be used for controlling the expression of a heterologous gene in mammalian cells and, advantageously, for obtaining specific expression in the cells of the vascular endothelium. The choice of the most suitable promoter from among the promoters in accordance with the invention depends on the level and specificity of expression which is needed.

The subject-matter of the present invention also encompasses recombinant nucleic acid molecules which contain at least one nucleic acid molecule according to the invention which is linked to at least one heterologous sequence.

Within the meaning of the present invention, "heterologous" in relation to a given sequence is understood as meaning any nucleic acid sequence other than those which are immediately adjacent to the said sequence in nature.

The subject-matter of the present invention particularly encompasses:

a) expression cassettes which include:
   a promoter which contains at least one nucleic acid molecule in accordance with the invention; the promoter can be the VE cadherin promoter or a chimeric promoter which includes at least one functional domain of the VE cadherin promoter,
   and a heterologous sequence which is placed under the transcriptional control of the said promoter.
b) recombinant vectors which include an insert which consists of a nucleic acid molecule in accordance with the invention. Advantageously, these vectors are expression vectors which include at least one expression cassette as defined above.

Large numbers of vectors into which it is possible to insert a nucleic acid molecule of interest in order to introduce the molecule into, and maintain it in, a eukaryotic or prokaryotic host cell are known per se; the choice of a suitable vector depends on the use which is envisaged for this vector (for example, replication of the sequence of interest, expression of this sequence, maintenance of the sequence in extrachromosomal form, or else integration into the chromosomal material of the host, etc.), as well as the nature of the host cell.

The invention furthermore relates to prokaryotic or eukaryotic cells which are transformed with at least one nucleic acid molecule according to the invention. Preferably, these cells are animal cells, in particular mammalian cells. The cells can be endothelial cells or cells of another cell type.

Transformed cells according to the invention can be obtained by any means, which are known per se, which enable a nucleic acid molecule to be introduced into a host cell. For example, in the case of animal cells, it is possible to use, inter alia, viral vectors (adenovirus, retrovirus, etc.) into which the sequence of interest has been previously inserted; it is also possible to combine the said sequence (which is either isolated or inserted into a viral or plasmid vector) with a substance, for example a liposome preparation, which enables it to cross the membrane of the host cells, or else to inject the sequence directly into the host cell.

Genes can, for example, be transferred into the vascular endothelium using recombinant adenoviruses or liposomes [NABEL E.G.; Circulation, 91, p. 541–548, (1995); VON DER LEYEN et al., Proc. Natl. Acad. Sci. USA, 92, p. 1137–1141, (1995); LARKIN et al., Transplantation, 61, p. 363–370, (1996)].

The inventors also obtained transgenic animals in which a heterologous gene was placed under the transcriptional control of the VE cadherin promoter and thereby established that the properties of this promoter, and in particular the specificity of expression in vascular endothelial cells, were exhibited in vivo as well as in vitro.

The present invention relates to animals, in particular non-human transgenic mammals, which are characterized in that all or part of their cells are transformed with a nucleic acid molecule according to the invention. The animals are, for example, animals into which a gene of interest has been introduced under the control of the VE cadherin promoter or of a chimeric promoter which has been constructed from the regulatory elements of this VE cadherin promoter which confer specificity of expression in the endothelial cells; the gene of interest is then only expressed in the cells of the vascular endothelium.

The transformed cells and the transgenic animals according to the invention can be used, in particular, as models for studying and/or modifying the expression of different genes in the endothelial cells.

The invention also relates to the use of nucleic acid molecules according to the invention for obtaining medicaments, in particular medicaments which are intended for treating pathologies such as arteriosclerosis or neoplastic diseases. For example, nucleic acid molecules according to the invention can be incorporated into medicaments which can be used, in particular, in gene therapy.

The present invention will be more fully understood with the aid of the remainder of the description, which follows and which refers to examples which describe the isolation and characterization of the VE cadherin promoter and functional domains of this promoter as well as their use for expressing a heterologous gene in cell cultures and in transgenic animals.

EXAMPLE 1
Cloning the VE Cadherin Promoter

The cloning of the murine VE cadherin gene, and the lambda 1 genomic clone which contains the region upstream of the first exon of this gene, have been previously described by HUBER et al. [Genomics, 32, p. 21–28 (1996)].

A 3653 bp SacI DNA fragment, which was derived from the lambda 1 genomic clone and which contained the first exon of the VE cadherin gene, 2813 bp of the 5' region and 782 bp of the beginning of the first intron, was inserted into the SacI site of pBluescript II SK+ (STRATAGENE). The sequence of each of the insert strands was determined by the Sanger method.

Different fragments of the 5' region were cloned into the expression vector pBLCAT3 [LUCKOW and SCHUTZ, Nucl. Acids Res. 15, p. 5490, (1987)] upstream of the CAT (chloramphenicol acetyltransferase) reporter gene.

For this purpose, a XhoI site was created immediately downstream of position +22 of the first exon by carrying out a PCR amplification using the above-described 3653 bp SacI fragment as the template and, as primers:

the following sequence:
(5'-CCCGGAAAGATCTGCTCTCT-3') (SEQ ID NO: 2), which contains a BglII site located at position −1190 of the 5' region, and
(5'-CTCCACTCGAGTCTGTCCAGGGCCGAGC-3') (SEQ ID NO: 3) which corresponds to the +6 to +22 sequence of the first exon, followed by the XhoI site.

The amplified fragment was digested with the enzymes XhoI and BglII and then inserted between the XhoI and BglII sites of pBLCAT3.

The resulting plasmid, which was designated "−1190", and whose insert was verified by sequencing, constitutes the starting point for all the CAT constructs mentioned below:

the "−515" construct was obtained by inserting the PvuII/XhoI fragment derived from "−1190" into the XbaI (treated with Klenow enzyme) and XhoI sites of pBLCAT3.

The "−289" construct was obtained by inserting the HindIII/XhoI fragment from the "−1190" construct into the HindIII and XhoI sites of pBLCAT3.

The "−187" construct was obtained by inserting the ApaI (treated with phage T4 DNA polymerase)/XhoI fragment derived from the "−1190" construct into the SalI (treated with Klenow enzyme) and XhoI sites of pBLCAT3.

The "−139" construct was obtained by inserting the PstI/XhoI fragments derived from "−1190" into the PstI/XhoI sites of pBLCAT3.

The "−5800" construct was obtained by inserting the EcoRI (treated with Klenow enzyme)/BglII fragment of lambda 1 into the SalI (treated with Klenow enzyme) and BglII sites of "−1190".

The "−2486" construct was obtained by inserting the SpeI/BglII fragment of lambda 1 into the XbaI (not filled-in) and XhoI sites of "−1190".

Furthermore, the following plasmids were constructed in order to be used as positive controls:

the plasmid which is here designated "HSVTK", which is similar to the pBLCAT2 construct described by LUCKOW and SCHUTZ (abovementioned publication) and which contains the CAT gene under the control of the promoter of the herpes virus thymidine kinase gene;

the plasmid which is here designated "RSV", which is identical to that described by GORMAN et al. [Proc. Natl. Acad. Sci. USA, 79, p. 6777–6781, (1982)] and which contains the CAT gene under control of the LTRs of the Rous sarcoma virus.

In addition, constructs which were derived from the above constructs by deleting the promoters controlling the expression of the CAT gene were used as negative controls.

A luciferase expression plasmid, containing the "luc+" gene (PROMEGA) inserted into the vector pCDNA3 (IN VITROGEN), was used for calibrating the measurements of CAT activity using the protocol described by HUBER et al. [J. Biol. Chem. 265, p. 5696–5701, (1990)].

These constructs were used for transfecting, on the one hand, bovine aorta endothelial cells ("BAEC"), which were derived from bovine aortas treated with collagenase [MOORE et al., Clin. Invest., 79, p. 124–130, (1987)], and, on the other hand, cells of the cell lines 3T3 ("NIH-3T3"; fibroblast cell line), HeLa (epithelial cell line), HepG2 (hepatocyte cell line), Hel and Lin 175 (hematopoietic cell lines), which were obtained from the ATCC.

In a first series of experiments, the CAT activity of the constructs containing the different restriction fragments obtained from the lambda genomic clone was determined in the cells of the BAEC and 3T3 cell lines using the HSVTK construct and the corresponding construct without promoter as controls.

In a second series of experiments, the CAT activity of the construct containing the −2486, +22 fragment was determined in the cells of the BAEC, 3T3, HeLa, HepG2, Hel and Lin 175 cell lines using the HSVTK construct, the RSV construct and the corresponding constructs without promoters as controls.

The cells were cultured in DMEM (GIBCO) containing 10% foetal calf serum (15% in the case of the BAEC cells).

The BAEC, 3T3, HeLa and HepG2 cells, which had been seeded the previous day ($10^6$ cells), were transfected with 3.5 picomoles of CAT construct and 5 micrograms of luceriferase-expressing plasmid using the calcium phosphate method [WIGLER et al., Cell., 11, p. 223–232, (1977)].

The Hel and Lin 175 cells ($10^7$ cells) were transfected with 3.5 picomoles of CAT construct, 10 micrograms of luciferase plasmid and 50 micrograms of salmon sperm DNA, as carrier, by means of electroporation (BIORAD GENE PULSER, adjusted to 400 V and 960 microfarads) in 0.8 ml of PBS.

In every case, the cell extracts were prepared 2 days after transfection by carrying out 3 cycles of freezing/thawing.

Prior to determining the CAT activity, the luciferase activity was determined on an aliquot of the cell extracts using a kit (PROMEGA) and a luminometer (LKB).

The results of the first series of experiments are shown in FIG. 1: the equivalent of 1200 and 3000 arbitrary light units of the cell extracts obtained from the BAEC and 3T3 cells, respectively, was used for determining the CAT activity.

The results reproduced in FIG. 1 represent the means of from 5 to 10 transfections carried out in duplicate.

The constructs containing the different fragments obtained from the lambda genomic clone are identified by the position of the 5' end of the fragment concerned (in relation to the transcription initiation site); "without prom" indicates the construct containing the CAT gene on its own; "HSVTK" indicates the positive control.

These results make it possible to establish:

1) that all the constructs (with the exception of the negative control) are significantly expressed in the endothelial cells; however, a decrease of approximately 50% is observed in the activity of the −515 to −5800 constructs as compared with that of the constructs ranging from −139 to −289

2) that, while the proximal constructs are active in the fibroblasts, this activity decreases progressively when the fragment is extended in order to become negligible and comparable to the background (construct without promoter) in the case of the −2486 and −5800 fragments. These two constructs can be regarded as being tissue-specific.

The second series of experiments was carried out using the construct containing the −2486, +22 fragment. The sequence of this fragment is depicted in the annexed sequence listing under the number SEQ ID NO: 1.

Figure 2:
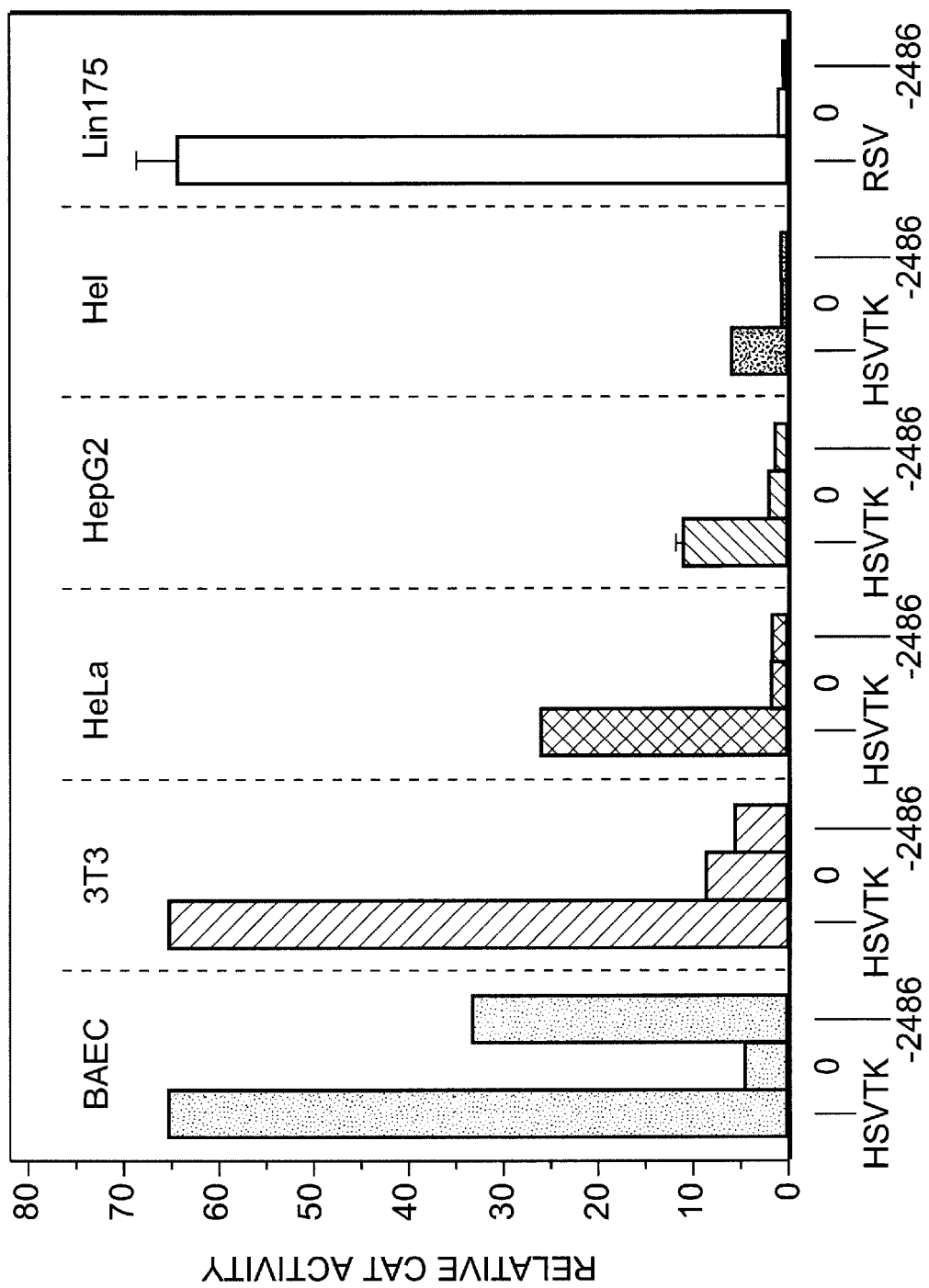
FIG. 2 depicts the CAT activity of the −2486, +22 fragment construct in various cell types.

The promoter activity of this construct was determined in various cell types. The results are shown in FIG. 2: the CAT activities were determined using the equivalent of 200 arbitrary light units in the case of Hel, 3000 units in the case of HepG2, 150 units in the case of HeLa and 200 units in the case of Lin175; 1200 units in the BAEC and 3000 units in the case of 3T3.

"−2486" indicates the construct containing the −2486, +22 fragment; "0" indicates the construct containing the CAT gene on its own; "HSVTK" and "RSV" indicate the positive controls.

These results confirm that the construct containing the −2486, +22 fragment is only active in the endothelial cells.

EXAMPLE 2
Production and Analysis of Transgenic Mice Which are Expressing a Reporter Gene Under the Control of the VE Cadherin Promoter A pBLCAT3 plasmid containing the −2486, +22 promoter, obtained as described in Example 1 above, was digested with the endonucleases SacI and SalI, and the resulting restriction fragment, which comprises the CAT gene and the −2486, +22 promoter, was purified. This fragment was injected into mouse eggs, which were reimplanted into pseudopregnant mice using the protocol described by HOGGAN et al. [Cold Spring Harbor Laboratory Press, (1994)].

The 2 founders obtained (line 28 and line 23) were genotyped by the Southern technique and the number of transgene copies in each of them was calculated by quantitative analysis using a PHOSPHORIMAGER (MOLECULAR DYNAMICS).

The CAT enzymic activity was measured on homogenates of different organs from adult animals descended (F1) from each of these 2 founders.

The results are shown in Table I below:

TABLE I

| Number of transgenes | Line 28<br>16 | Line 23<br>8 |
|---|---|---|
| | CAT[a] activity | |
| Heart | 440 (1) | 85.3 (1) |
| Liver | 162 (0.37) | 25.7 (0.30) |
| Brain | 252 (0.57) | 50.6 (0.59) |
| Lung | 1298 (2.95) | 275 (3.22) |
| Spleen | 148 (0.34) | 21.2 (0.25) |
| Kidney | 168 (0.38) | 22.6 (0.26) |
| Thymus | 145 (0.33) | 12.9 (0.15) |
| Skin | 169 (0.38) | 19.7 (0.23) |
| Blood cells | <0.01 | <0.01 |
| Plasma | 0.5 (0.0011) | 0.63 (0.007) |

[a]in pmol of chloramphenicol acetylated per hour and per µg of protein extract; the relative activity as compared with the heart is indicated in brackets.

A strong CAT activity is observed, with this activity being positively correlated with the degree of vascularization of the tissues concerned and with the number of copies of the transgene in each line. only the blood cells fail to exhibit any detectable activity. Furthermore, the expression profile observed in the two lines of transgenic mice is identical, a fact which makes it possible to exclude any potential influence of the integration site on expression of the transgene. This demonstrates the tissue-specific character in vivo of the expression which is controlled by the promoter of the VE cadherin gene.

The location of the CAT expression in the transgenic mice was also studied by means of immunohistochemistry.

13.5-day-old embryos were removed, fixed for 2 h in 4% paraformaldehyde in PBS and then incubated at 22° C. for 1 h in PBS/15% sucrose buffer; they were then incubated overnight in PBS/30% sucrose and finally frozen in OCT (TISSUTEK) using a dry ice/ethanol bath. 10 micrometre parasagittal sections, which were prepared using a cryostat (LEICA), were dried at 45° C. for 5 min and fixed once again for 30 min in PBS/4% paraformaldehyde; they were then incubated with different anti-CAT, anti-VE cadherin and anti-PECAM-1 (platelet endothelial cell adhesion molecule 1, used here as an endothelial marker) antibodies. The antigen/antibody complexes are visualized with a second, labelled antibody under the conditions summarized in Table II below.

TABLE II

| Labelled protein | First antibody | Incubation conditions | Second antibody | Incubation conditions |
|---|---|---|---|---|
| CAT | IgY (PROMEGA) dil. 1/300 | 4° C. for 16 h | FITC-labelled anti-IgY (PROMEGA) dil. 1/100 | 22° C. for 1 h |
| VE cadherin | rabbit serum dil. 1/300 | 4° C. for 16 h | TRITC-labelled anti-rabbit IgG (JACKSON) dil. 1/100 | 22° C. for 1 h |
| PECAM 1 | rat monoclonal, pure hybridoma supernatant | 4° C. for 16 h | FITC-labelled anti-rat IgG JACKSON dil. 1/100 | 22° C. for 1 h |

Examination of the histological sections after visualization shows that expression of the CAT protein is restricted to the endothelium and enables a colocalization to be observed between the CAT and the endogenous VE cadherin as well as between the CAT and the PECAM-1.

What is claimed is:

1. An isolated nucleic acid molecule which confers a specificity of expression to cells of the vascular endothelium, wherein said nucleic acid molecule is selected from the group consisting of the VE cadherin promoter of SEQ ID NO: 1 and a fragment thereof comprising the sequence extending from position +22 to position −1190 in relation to the transcription initiation site of the mouse VE cadherin gene.

2. An expression cassette, comprising a promoter which contains at least one nucleic acid molecule according to claim 1 and a heterologous sequence of interest which is placed under transcriptional control of said promoter.

3. A recombinant vector which comprises an insert which consists of the nucleic acid molecule according to claim 1 or the expression cassette according to claim 2.

4. An isolated cell which is transformed with at least one of: the nucleic acid molecule according to claim 1 or the expression cassette according to claim 2.

5. A method of expressing a gene of interest in an isolated mammalian endothelial cell comprising:
   (a) providing a vector comprising the expression cassette of claim 2, and
   (b) introducing said vector directly in said endothelial cell.

6. A method of expressing a gene of interest in a mammalian endothelial cell, comprising the steps of:
   culturing said endothelial cell in vitro,
   providing a vector comprising the expression cassette of claim 2, and
   introducing said vector directly in said endothelial cell; thereby expressing said gene of interest in said mammalian endothelial cell.

7. The recombinant vector of claim 3 wherein the vector is viral in origin.

8. A composition comprising the vector of claim 3 and a liposome carrier.

9. An isolated cell which is transformed with the recombinant vector according to claim 3.

10. The transformed cell according to claim 9, wherein said cell is a mammalian cell.

11. The transformed mammalian cell of claim 10, wherein said cell is an endothelial cell.

12. A transformed cell according to claim 4, wherein said cell is a mammalian cell.

* * * * *